United States Patent [19]

Ahnfelt-Ronne et al.

[11] Patent Number: 5,110,819
[45] Date of Patent: May 5, 1992

[54] SUBSTITUTED QUINOLINES AND MEDICINAL USE THEREOF

[75] Inventors: Ian Ahnfelt-Ronne; Erik T. Hansen, both of Fredensborg; Dorte Kirstein, Lyngby; Ole Bent I. Nielsen; Schneur Rachlin, both of Vaerlose, all of Denmark

[73] Assignee: Leo Pharmaceutical Products Ltd., Ballerup, Denmark

[21] Appl. No.: 476,403

[22] PCT Filed: Nov. 17, 1988

[86] PCT No.: PCT/DK88/00188
§ 371 Date: Jun. 1, 1990
§ 102(e) Date: Jun. 1, 1990

[87] PCT Pub. No.: WO89/05294
PCT Pub. Date: Jun. 15, 1989

[30] Foreign Application Priority Data

Dec. 1, 1987 [GB] United Kingdom ............... 8728051

[51] Int. Cl.⁵ ............... C07D 403/10; C07D 413/10; A61K 31/47
[52] U.S. Cl. ............... 514/311; 514/232.5; 514/314; 546/174; 546/176; 544/128
[58] Field of Search ............... 546/174, 176; 514/311, 514/314, 232.5; 544/128

[56] References Cited

U.S. PATENT DOCUMENTS

| | | | |
|---|---|---|---|
| 4,826,987 | 5/1989 | Nielsen et al. | 546/174 |
| 4,904,786 | 2/1990 | Musser et al. | 546/176 |
| 4,929,626 | 5/1990 | Mohrs et al. | 546/174 |

FOREIGN PATENT DOCUMENTS

| | | |
|---|---|---|
| 0206751 | 12/1986 | European Pat. Off. |
| 0219308 | 12/1986 | European Pat. Off. |
| 0200101 | 4/1988 | European Pat. Off. |
| 0232954 | 11/1988 | European Pat. Off. |
| 0315399 | 5/1989 | European Pat. Off. |
| 2578540 | 12/1986 | France |

*Primary Examiner*—David B. Springer
*Attorney, Agent, or Firm*—Cushman, Darby & Cushman

[57] ABSTRACT

The present invention relates to hitherto unknown compounds of formula, in which formula $R_1$ stands for hydrogen, straight or branched, saturated or unsaturated, unsubstituted or substituted $C_1$—$C_8$—alkyl, aryl or for ar—$C_1$—$C_4$—alkyl, aryl or an being unsubstituted or substituted phenyl, $R_2$, $R_3$, $R_4$, $R_5$, $R_6$ and $R_7$ are the same or different and stand for hydrogen, halogen, pseudo halogen, cyano, nitro, amino, carboxy, carbalkoxy, carbamyl, hydroxy, alkyl, alkoxy; n and m are the same or different and stand for an integer from 0-6; provided that n cannot be zero when A stands for carboxy and X and Q both stand for a bond; X stands for a bond or for O, S, S(O), $S(O)_2$ or for $NR_8$ where $R_8$ is defined as $R_1$ above; Q stands for a bond of for straight or branched, $C_1$—$C_6$—alkylene; A stands for an acidic group, e.g. for carboxy, 1H-tetrazolyl, a sulphonic acid group, a sulfamyl group, a sulphinic acid group or a hydroxamic acid group. The present compounds are of value in the human and veterinary practice as lipoxygenase inhibitors and/or leukotriene antagonists.

6 Claims, No Drawings

SUBSTITUTED QUINOLINES AND MEDICINAL USE THEREOF

The present invention relates to hitherto unknown compounds useful in the human and veterinary therapy, to pharmaceutically acceptable salts thereof, to bioreversible derivatives thereof, to methods for producing said new compounds, to pharmaceutical compositions containing the new compounds, to dosage units of the compositions, and to methods of treating patients using said compositions and dosage units.

It has recently been discovered that leukotrienes, which are formed via the 5-lipoxygenase pathway of arachidonic acid metabolism, are implicated in a variety of pathophysiologic functions, such as bronchoconstriction, plasma exudation, coronary artery spasm, leukocyte chemotaxis and neutrophil degranulation (1). It is therefore of considerable interest to develop compounds which inhibit 5-lipoxygenases and thereby the production of leukotrienes, or antagonize the effects of leukotrienes.

(1) P. J. Piper and M. N. Samhoun, Br.Med.Bull. 43 (1987) 297.

German patent application DE 3607 382 (corresponding to United Kingdom patent application No. 8604183) describes a series of pyridylmethoxy or -methyl-thio substituted N-substituted aniline derivatives with activities as lipoxygenase inhibitors and/or leukotriene antagonists. The N-substituent in these compounds may be substituted or unsubstituted aryl or aralkyl.

EP-A-206751 discloses compounds having the formula:

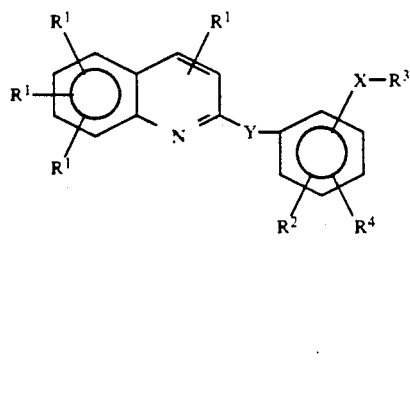

In this formula Y inter alia may be $CH_2O$, X is O, S, SO, $SO_2$ or $NR_2$ and $R^3$ inter alia may be a saturated or unsaturated aliphatic group which may be substituted by a carboxyl group. These compouns are described to antagonize the effects of the leukotrienes and to inhibit the leukotrienes. Thus, these compounds are valuable in the prevention and treatment of disease states in which the leukotrienes are the causative factor.

EP-A-190 722 discloses compounds of the formula:

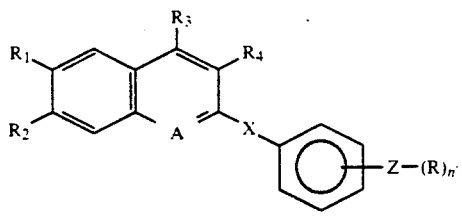

in which X is inter alia $CH_2O$, Z is an alkylene chain containing up to 10 carbon atoms in the principal chain which may be attached to the phenyl group through an oxygen atom and R may be $OR_6$ wherein $R_6$ is H, lower alkyl or phenyl. These compounds are lipoxygenase inhibitors possessing anti-inflammatory and anti-allergic activities.

EP-A-232 954 discloses compounds of the general formula:

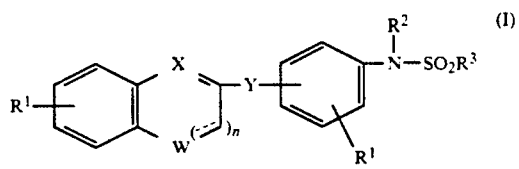

in which inter alia X may be an nitrogen atom and W a carbon atom, Y may be $CH_2O$, $R_2$ is hydrogen oder lower alkyl and $R_3$ is lower alkyl, perfluoro lower alkyl or perfluorophenyl. These compounds are useful in the treatment of leukotriene-mediated naso-bronchial obstructive air passage way conditions, such as allergic rhinitis, allergic bronchial asthma and the like, and antithrombotic therapy.

EP-A-233 763 discloses compounds of the formula:

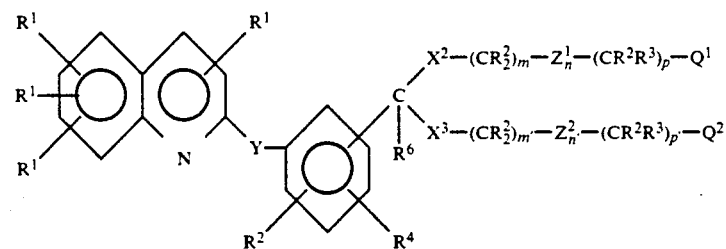

in which inter alia Y is $CH_2O$, and $X^2$ and $X^3$ are independently O, S, SO or $SO_2$ and $R^6$ is H or $C_1$ bis $C_4$ alkyl. The residues attached to $X_2$ and $X_3$ may be saturated or unsaturated aliphatic groups which may be inter alia substituted by a carboxyl group. These compounds are leukotriene antagonists or inhibitors and are useful for treatment of disease states in which the leukotrienes are the causative factor.

EP-A-271 287 has a similar disclosure.

Now it has surprisingly turned out that introduction of one of a number of acidic groups into such N-substituents results in compounds with an even more pronounced effect.

Furthermore, it has been found that in the presence of such acidic groups also compounds which are not anilines, but in which the nitrogen atom has been separated from the phenyl group with a carbon chain are potent compounds.

Moreover, these compounds are more specific agents, as their leukotriene antagonistic activity is much more pronounced than their activity as lipoxygenase inhibitors.

Also, the present compounds are well absorbed after enteral administration.

The present compounds have the formula I

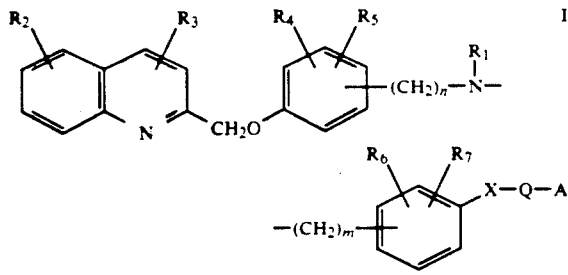

in which formula I $R_1$ stands for hydrogen, straight or branched, saturated or unsaturated, unsubstituted or substituted $C_1-C_8$-alkyl, aryl or for ar-$C_1-C_4$-alkyl, aryl or ar being unsubstituted or substituted phenyl, the above substitution being one or more of the following substituents: halogen, pseudo halogen, such as trifluoro methyl, cyano, nitro, amino, *carboxy, carbalkoxy, carbamyl, hydroxy, alkyl, alkoxy; $R_2$, $R_3$, $R_4$, $R_5$, $R_6$ and $R_7$ are the same or different and stand for hydrogen, halogen, pseudo halogen, cyano, nitro, amino, *carboxy, carbalkoxy, carbamyl, hydroxy, alkyl, alkoxy; n and m are the same or different and stand for an integer from 0-6; provided that n cannot be zero when A stands for carboxy and X and Q both stand for a bond; X stands for a bond or for O, S, S(O), S(O)$_2$ or for NR$_8$ where R$_8$ is defined as $R_1$ above; Q stands for a bond or for straight or branched, $C_1-C_6$-alkylene; A stands for an acidic group, e.g. for carboxy, 1H-tetrazolyl, a sulphonic acid group, a sulfamyl group, a sulphinic acid group or a hydroxamic acid group.
\* substituted amino Among the preferred compounds of the invention are those of formula I, in which —X—Q—A stands for a carboxy-$C_1-C_6$-alkoxy or a 1H-tetrazolyl group.

Especially preferred compounds are:

3-(2'-quinolylmethoxy)-N-(3"-carboxymethoxybenzyl-)aniline;

3-(2'-quinolylmethoxy)-N-(2"-carboxymethoxybenzyl-)aniline;

3-(2'-quinolylmethoxy)-N-(4"-carboxymethoxybenzyl-)aniline;

3-(2'-quinolylmethoxy)-N-(4"-(1-carboxyethoxy)benzyl)aniline;

3-(2'-quinolylmethoxy)-N-(2"-carboxy-(3-propyloxy)-benzyl)aniline;

3-(2'-quinolylmethoxy)-N-(4"-(1H-tetrazolyl)benzyl-)aniline;

3-(2'-quinolylmethoxy)-N-(3"-(1H-tetrazolyl)benzyl-)aniline 3-(2'-quinolylmethoxy)-N-(4"-(1H-tetrazolyl)(3-propyloxy)benzyl)aniline;

3-(2'-quinolylmethoxy)-N-(3"-fluorobenzyl)-N-(4'''-hydroxaminocarbonylbenzyl)aniline.

The present salts of the compounds of formula I may be formed with pharmaceutically acceptable inorganic or organic acids, such as hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic limiting for the invention.

The present salts of the compounds of formula I may also be formed with pharmaceutically acceptable, inorganic or organic bases. As examples of salts formed with pharmaceutically acceptable, non-toxic bases, mention may be made of alkali metal salts and alkaline earth metal salts, such as lithium, sodium, potassium, magnesium, calcium salts, as well as salts with ammonia and suitable non-toxic amines, such as $C_1-C_6$-alkylamines, e.g. triethylamine, $C_1-C_6$-alkanolamines, e.g. diethanolamine or triethanolamine, procaine, cycloalkylamines, e.g. dicyclohexylamine, benzylamines, e.g. N-methylbenzylamine, N-ethylbenzylamine, N-benzyl-β-phenethylamine, N,N'-dibenzylethylenediamine or dibenzylamine, and heterocyclic amines, e.g. morpholine, N-ethylpiperidine and the like.

Even if the present compounds are well absorbed after enteral administration, in some cases it can be advantageous to prepare suitable bioreversible derivatives of compounds of the invention, i.e. to prepare so-called prodrugs, preferably derivatives, the physiochemical properties of which leads to improved solubility at physiological pH and/or absorption of the compound in question.

Such derivatives are for instance esters of N-hydroxymethyl derivatives of compounds of the invention, such compounds being prepared by reaction of a secondary aminefunction of compounds of the invention with formaldehyde (2,3,4,5) followed by reaction with a suitable acidic compound or activated derivatives of such compounds, for instance with bisulfite (6), N,N-dimethylglycine, N,N-diethyl-β-alanine, or phosphoric acid (7), but other suitable acids which form bioreversible derivatives with desirable physicochemical properties can be used as well.

(2) R. G. Kallen and W. P. Jencks, J. Biol. Chem. 241 (1966) 5864.
(3) C. J. Martin and M. A. Marini, J. Biol. Chem. 242 (1967) 5736.
(4) M. Levy and D. E. Silberman, J. Biol. Chem. 118 (1937) 723.
(5) S. Lewin and D. A. Humphany, J. Chem. Soc. B (1966) 210.
(6) B. C. Jain, B. H. Iyer, and P. C. Guha, Science and Culture 11 (1946) 568.
(7) S. A. Varia, S. Schuller, K. B. Sloan and V. J. Stella, J. Pharm. Sci., 73 (1985) 1068 and following papers.

Further examples include esters formed with the acidic function in the molecule, such as acyloxyalkyl, alkoxycarbonyloxyalkyl or aminoacyloxyalkyl esters, which are readily hydrolyzed in vivo or in vitro.

Among the above esters the following are preferred: alkanoyloxymethyl with from 3 to 8 carbon atoms, 1-alkanoyloxy)ethyl with from 4 to 9 carbon atoms, alkoxycarbonyloxymethyl with from 3 to 6 carbon atoms, 1-(alkoxycarbonyloxy)ethyl with from 4 to 7 carbon atoms, and α-aminoalkanoyloxymethyl with from 2 to 6 carbon atoms.

Other preferred esters are lactonyl esters, e.g. 3-phthalidyl, 4-crotonolactonyl or γ-butyrolacton-4-yl esters.

Also within the scope of the invention are methoxymethyl, cyanomethyl, or mono- or dialkyl substituted aminoalkyl esters, e.g. 3-dimethylaminoethyl, 2-diethylaminoethyl, or 3-dimethylaminopropyl esters.

In particular, such esters are preferred which are well absorbed upon enteral administration and during or after the absorption are hydrolysed to the compounds of formula I.

These examples are not to be considered as limiting for the invention, and other suitable methods to improve the physicochemical properties and solubility of the compounds concerned can be used as well.

Metabolites of arachidonic acid include prostaglandins and leukotrienes. Both of these two groups of metabolites are important in the pathophysiology of inflammatory and allergic reactions. Many inhibitors of prostaglandin synthesis are known and are being used as anti-inflammatory agents (8), but relatively few leukotriene inhibitors are presently known, and they are generally not clinically acceptable. The first step in the biochemical synthesis of all leukotrienes is the peroxidation at the 5-carbon atom of arachidonic acid. This reaction is catalyzed by the enzyme 5-lipoxygenase, present mainly in leukocytes. Leukotriene $B_4$ is one of the most potent chemoattractants for polymorphonuclear leukocytes, and at the same time causes aggregation and degranulation of these inflammatory cells. It is thus a potent pro-inflammatory hormone. Leukotriene $C_4$, $D_4$, and $E_4$ together comprise the agent known previously as "slow-reacting substance of anaphylaxis" (SRS-A), which is three orders of magnitude more potent than histamine in causing bronchoconstriction, and also regulates microvascular smooth muscle contractility and permeability. It is therefore a mediator of asthmatic, allergic and inflammatory reactions.

(8) R. J. Flower, S. Moncada and J. R. Vane, in: The Pharmacological Basis of Therapeutics (1980), eds. A. G. Gilman, L. S. Goodmann and A. Gilman), (Macmillan, New York) p. 682.

Inhibition of 5-lipoxygenase thus leads to a decrease in the formation of all of these inflammatory and allergic mediators. This has very important clinical implications, as specific 5-lipoxygenase inhibitors and leukotriene antagonists are of potential interest in the therapy of asthma, allergy, rheumatoid arthritis, spondyloarthritis, gout, atherosclerosis, proliferative and inflammatory skin-disorders, such as psoriasis and atopic dermatitis, chronic inflammatory bowel disease, and other inflammatory conditions, vasospasm associated with angina pectoris, pulmonary hypertension, cystic fibrosis, the adult respiratory distress syndrome, ischemic and reperfusion injury etc. (9). The identification of specific 5-lipoxygenase inhibitors and leukotriene antagonists is thus a novel approach with very wide implications for the treatment of a diversity of clinical disorders.

(9) E. G. Goetzl, D. G. Payan and D. W. Goldman, J. Clin. Immunol. 4 (1984) 79.

The following method was used to assay 5-lipoxygenase activity in vitro: Rat peritoneal cells were harvested by i.p. injection of 10 ml Hank's balanced salt solution (GIBCO, cat. No. 4025, U.S.A.) containing 12.5 U/ml sodium heparin (Leo, Denmark) in anaesthesized rats. The resulting cell suspension, which mainly contained macrophages, was transferred to a test tube and washed twice by centrifugation (200 g, 10 min.) and resuspended in Hank's balanced salt solution containing 0.5% bovine serum albumin (BSA) (Sigma Chem. Co., U.S.A.). The cells from 9 rats were finally resuspended in Hank's balanced salt solution (with BSA) containing 5 $\mu$Ci [1-$^{14}$C]arachidonic acid (The Radiochemical Centre, Amersham, U.K.) and incubated for 90 minutes at 37° C. This caused labelling of cell membrane phospholipids as radioactive arachidonic acid was incorporated in the 2-position of the glycerol moiety. Excess arachidonic acid was then removed by washing the cells twice as described above. The cells were finally resuspended in the same solution (without BSA) at $10^7$ cells/ml. 475 $\mu$l of the cell suspension was preincubated at 37° C. for 5 minutes with either 5 $\mu$l dimethylsulphoxide (DMSO) (control tube), or 5 $\mu$l of a drug solution in DMSO. Then 20 $\mu$l of a mixture of equal volumes of the calcium ionophore A23187, $10^{-4}$M in ethanol (Calbiochem, U.S.A.), and 0.4M $CaCl_2$ in water was added. The final concentration of A23187 was thus $2 \times 10^{-6}$M, and of $Ca^{++}$ 8 mM. After 5 minutes of incubation the tubes were transferred to an ice-bath and centrifuged for 10 minutes at 3,000 g (4° C.). An aliquot of the supernatant was counted by liquid scintillation spectrometry in order to calculate the total radioactive release induced by A23187 in presence of drugs. A decrease in radioactive release was taken as indication of phospholipase $A_2$ inhibition. The supernatant was then extracted with ethyl acetate (2 ml), adjusted to pH 3 with 1N HCl and further extracted with 2 ml ethyl acetate. The combined extracts were evaporated to dryness in vacuo, the residue was redissolved in a small volume of methanol and applied by means of a Desaga Autospotter ™ to a silica-gel coated thin-layer plate fitted with a polar concentrating zone (Merck Art. 11798, Darmstadt, F.R.G.). The plates were developed in the organic layer of the solvent mixture ethyl acetate/acetic acid/isooctane/water (55:10:25:50). Radioactive spots were detected by autoradiography (AGFA-GEVAERT, Osray-RPI X-ray film, Belgium), and changes induced by drugs in the metabolic pattern of arachidonic acid were quantified by a laser densitometer (LKB, Ultroscan ™ 2202, Bromma, Sweden) in combination with an integrating computer (SP 4100, Spectra-Physics, San Jose, Calif., U.S.A.).

These cells produced measurable amounts of radioactive 6-keto-prostaglandin $F_{1\alpha}$, thromboxane $B_2$, prostaglandin $D_2$, hydroxyheptadecatrienoic acid (HHT) (all cyclooxygenase products), 5-hydroxyeicosatetraenoic acid (5-HETE) and leukotriene $B_4$ (both 5-lipoxygenase products).

When a compound produced according to one of the Examples 2, 8, 9, 11, 12, 13, 14, 16, 20, 21 or 22 at a final concentration of $10^{-6}$M was added to the reaction mixture described above, a significant and specific decrease in the production of leukotriene $B_4$ and 5-HETE occurred. At the same time, a decrease in synthesis of the cyclooxygenase products HHT, prostaglandin $D_2$, thromboxane $B_2$ and 6-keto-prostaglandin $F_{1\alpha}$ was not observed. This pattern of drug activity is indicative of truly specific 5-lipoxygenase inhibition.

Leukotriene antagonists may be identified by observing the contractions elicited in preparations of guinea-pig ileum strips suspended in a physiological buffer by addition of pure leukotriene $D_4$ (LTD$_4$) (10). The ileum strips are connected to an isotonic transducer, and the contractions are continuously recorded on a multichannel recorder. Before addition of LTD$_4$, atropine and indomethacin are added to the buffer in order to block any cholinergic or prostaglandinmediated contractile effects. Test compounds to be studied with respect to leukotriene antagonism are dissolved in DMSO and added to the organ bath 2 minutes prior to addition of LTD$_4$ at $10^{-9}$M (final concentration), the final concentration of DMSO being 0.1%, a concentration which can be shown not to affect the ileum response to LTD$_4$. The test compounds may be added at various concentrations, often beginning at $10^{-6}$M and then decreasing the concentration in case of antagonism.

(10) I. Ahnfelt-Ronne, D. Kirstein and C. Kaergaard-Nielsen, European J. Pharmacol. 155 (1988) 117.

When the compounds of the present invention were added to the ileum preparation before addition of LTD$_4$ a significant inhibition occurred of the specific LTD$_4$-induced contraction. In several cases this inhibition occurred at concentrations in the submicromolar range, e.g. with a compound according to one of the Examples 1 to 6 or 8 to 19 or 21 to 22 (all Examples except 7 and 20). On the other hand, contractions induced with histamine at $10^{-7}$M were not inhibited by these compounds even at micromolar concentrations.

Leukotrine antagonists may be further characterized using guinea-pig tracheal strips instead of ileum strips (10). In this relevant in vitro model of human airways (11) tracheal strips are suspended in a physiological buffer containing indomethacin. A concentration-response curve to $LTD_4$ is generated in the presence and absence of the leukotriene antagonist. From these curves the potency of a leukotriene antagonist may be expressed as the $pK_B$ value, the negative logarithm of the antagonist dissociation constant. The $pK_B$ value is determined as $-\log$ ([antagonist]/(dose ratio $-1$)), where the dose ratio is defined as $EC_{50}$ (pressence of antagonist)/$EC_{50}$ (absence of antagonist) and $EC_{50}$ refers to the concentration of $LTD_4$ eliciting 50% of the maximum response to $LTD_4$ (12). This is the generally accepted way of expressing leukotriene antagonistic potency independent of $LTD_4$ concentration. $pK_B$ values for the compounds according to the Examples 1, 9 and 10 were found to be 8.3, 9.5 and 8.4, respectively.
(11) R. M. Muccitelli, S. S. Tucker, D. W. P. Hay, T. J. Torphy and M. A. Wasserman, J. Pharmacol. Exp. Ther. 243 (1987) 467.
(12) R. F. Furchgott, in: Handbook of Experimental Pharmacology, vol 33 (1972), eds. O. Eichler, A. Farah, H. Herken and A. D. Welch (Springer Verlag, New York) p. 283.

It is of importance to investigate the receptor binding properties of leukotriene antagonists in relation to their $pK_B$ values (13), i.e. to correlate antagonist receptor blocking with inhibition of smooth muscle contraction. Receptor binding studies may be performed with guinea-pig lung membranes in a direct competition assay between a leukotriene antagonist and [$^3$H]$LTD_4$ for binding to the $LTD_4$ receptor (10,13). A $pIC_{50}$ value is determined as the negative logarithm of the molar concentration of antagonist inhibiting [$^3$H]$LTD_4$ binding by 50%. $pIC_{50}$ values for the compounds according to the Examples 1, 9 and 10 were found to be 7.3, 8.1 and 7.5, respectively. These $pIC_{50}$ values were observed to correlate with the antagonist $pK_B$ values, proving that the inhibition of smooth muscle contraction by the present compounds in fact depends mechanistically on binding to the $LTD_4$ receptor.
(13) S. Mong, H.-L. Wu, M. O. Scott, M. A. Lewis, M. A. Clark, B. M. Weichman, C. M. Kinzig, J. G. Gleason and S. T. Crooke, J. Pharmacol. Exp. Ther. 234 (1985) 316.

The present invention also relates to a method for producing the present compounds.

In one embodiment, an amine of the formula II

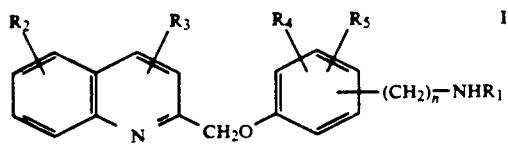

in which $R_1$, $R_2$, $R_3$, $R_4$, $R_5$ and n have the above meanings, is reacted with a compound of the formula III

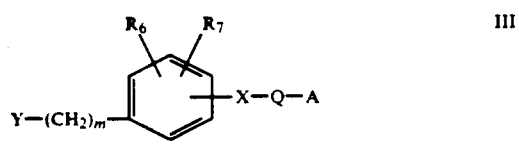

in which $R_6$, $R_7$, X, Q, A and m have the above meanings, and Y is capable of forming a "good leaving group", Y thus standing for e.g. a halogen atom, such as chlorine, bromine or iodine, or an alkyl- or arylsulphonyloxy group, but other leaving groups can be used as well, such as an alkylsulphate group, a chlorosulphonyloxy group, an alkylsulphite group, a mono- or dialkylphosphate group or a nitrate group, to form a compound of the formula I.

The reaction is performed in a suitable inert organic solvent, such as methanol, ethanol, dimethylformamide or hexamethyl phosphoric triamide, but other solvents can be used as well; the reaction is performed at a temperature about or above room temperature, up to the boiling point of the solvent used. In some cases it can, however, be convenient to cool the reaction mixture below room temperature, depending on the nature of the compound of the formula III used. The reaction is also conveniently performed in the presence of an organic base, such as pyridine, triethylamine, sodium methanolate or sodium ethanolate or in the presence of a suitable inorganic base, such as an alkalimetal hydroxide, an alkalimetal carbonate or an alkalimetal hydrogen carbonate, but other bases can be used as well. The crude reaction products of the formula I are collected by filtration, if convenient after dilution with e.g. water, or are extracted from the reaction mixture with a suitable solvent, such as diethyl ether, ethyl acetate, dichloromethane or chloroform. The products are purified e.g. by recrystallization or by chromatography, if convenient after conversion to salts with suitable inorganic or organic acids as defined above.

In another embodiment, an amine of the formula II in which $R_1$ stands for hydrogen is converted to a compound of the formula I, in which $R_1$ stands for hydrogen by reductive alkylation, e.g. by reaction with a carbonyl compound of the formula IV

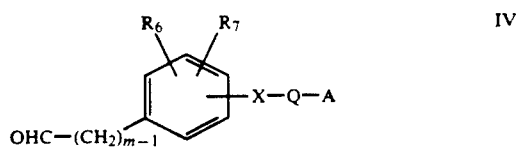

in which $R_6$, $R_7$, X, Q, A and m have the above meanings, followed by hydrogenation in the presence of a suitable catalyst or by reduction e.g. with an alkalimetal borohydride. The hydrogenation or reduction can, if convenient, be performed simultaneously with the reaction with the carbonyl compound, that is, without isolation of the intermediary, so called Schiff-base.

The reaction is performed in a suitable inert organic solvent, such as methanol or ethanol, but other solvents can be used as well. The reaction is preferably performed at ambient temperature, but in some cases it is convenient to cool the reaction mixture below room temperature, or to heat the reaction mixture above room temperature, up to the boiling point of the solvent used, depending on the nature of the reactants of the formulae II and IV used. The isolation and purification of the products can be performed as described above.

In still another embodiment a compound of the formula V

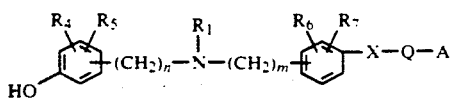

in which $R_1$, $R_4$, $R_5$, $R_6$, $R_7$, X, Q, A, n and m have the above meanings, is reacted with a compound of the formula VI

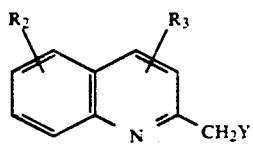

in which $R_2$, $R_3$ and Y have the above meanings, to form the desired compound of formula I.

The solvent and reaction conditions used are conveniently as described above for the alkylation of amines of the formula II, but other solvents and/or reaction conditions can be used as well, depending on the nature of the compounds of formulae V and VI which are reacted.

In a further embodiment a compound of the formula VII

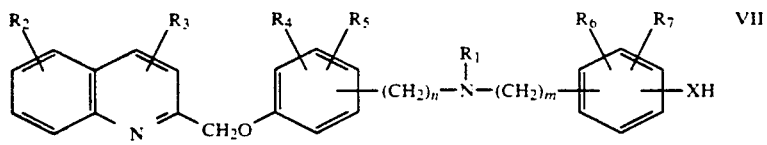

in which $R_1$, $R_2$, $R_3$, $R_4$, $R_5$, $R_6$, $R_7$, n and m have the above meanings, and X stands for O, S or $NHR_8$, where $R_8$ has the above meanings, is reacted with a compound of the formula VIII

Y—Q—A  (VIII)

in which A, Q, and Y have the above meanings, to form the desired compound of formula I.

The solvent and reaction conditions used are conveniently as described above for the alkylation of amines of the formula II, but other solvents and/or reaction conditions can be used as well, depending on the nature of the compound of the formulae VII and VIII which are reacted.

Additionally, the acidic functionalities A can be prepared according to the following general reaction schemes:

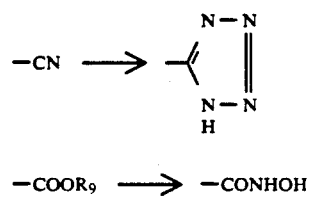

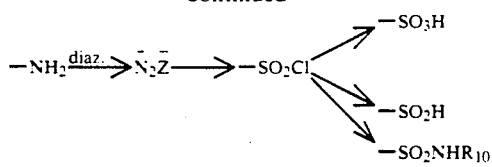

$R_{10}$ having the same meanings as $R_1$.

The present compounds are intended for use in pharmaceutical compositions which are useful in the treatment of the above mentioned diseases.

The amount required of a compound of formula (I) (hereinafter referred to as the active ingredient) for therapeutic effect will, of course, vary both with the particular compound, the route of administration and the mammal under treatment. A suitable dose of a compound of formula (I) for a mammal suffering from e.g. an inflammatory condition as defined hereinbefore is 0.5 to 100 mg per kilogram bodyweight, the most preferred dosage being 0.5 to 50 mg/kg of mammal bodyweight, for example 5 to 25 mg/kg; administered once or more times daily.

In the case of the treatment or prophylaxis of inflammatory airway conditions, a suitable anti-asthmatic dose of a compound of formula (I) is 1 μg to 50 mg of compound per kilogram bodyweight, the most preferred dosage being 1 μg to 10 mg/kg of mammal bodyweight, for example from 1 μg to 5 mg/kg.

While it is possible for an active ingredient to be administered alone as the raw chemical, it is preferable to present it as a pharmaceutical formulation. Conveniently, the active ingredient comprises from 0.1% to 100% by weight of the formulation. Conveniently, dosage units of a formulation contain between 0.1 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such self-propelling powder-dispensing formulations described hereinafter), may comprise 0.1 to 20% w/w, for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), intra-articular, topical nasal or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredient. Compressed tablets may be prepared by compressing, in a suitable machine, the active ingredient in a free-flowing form, such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations, such as liniments, lotions, applications; oil-in-water or water-in-oil emulsions, such as creams, ointments or pastes; or solutions or suspensions, such as drops. For example, for ophthalmic administration, the active ingredient may be presented in the form of aqueous eye drops as, for example, a 0.1-1.0% solution.

Formulations suitable for administration to the nose or buccal cavity include powder, self-propelling and spray formulations, such as aerosols and atomizers. The formulations, when dispersed, preferably have a particle size in the range of 10 to 100µ.

Such formulations are most preferably in the form of a finely comminuted powder for pulmonary administration from a powder inhalation device or self-propelling powder-dispensing formulations, where the active ingredient, as a finely comminuted powder, may comprise up to 99.9% w/w of the formulation. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$-$C_6$-alkyl hydrocarbons or halogenated $C_1$-$C_6$-alkyl hydrocarbons or mixtures thereof; chlorinated and flourinated $C_1$-$C_6$-alkyl hydrocarbons are especially preferred. Generally, the propellant constitutes 50 to 99.9% w/w of the formulation whilst the active ingredient constitutes 0.1 to 20% w/w, for example about 2% w/w, of the formulation.

The pharmaceutically acceptable carrier in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are esters and partial esters of fatty acids with aliphatic polyhydric alcohols, for instance, sorbitan monooleate and sorbitan trioleate, known commercially as "Span 80" (Trade Name) and "Span 85" (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms). The solid anionic surfactants may constitute from 0.01 up to 20% w/w of the formulation, though preferably below 1% w/w of the composition. Solid diluents may be advantageously incorporated in such self-propelling formulation where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present as such in suspension or in solution. Such self-propelling formulations may comprise the active ingredient, propellant and co-solvent, and advantageously an anti-oxidant stabiliser. The propellant is one or more of these already cited above. Co-solvents are chosen for their solubility in propellant, their ability to dissolve the active ingredient, and for their having the lowest boiling point consistent with these above-mentioned properties. Suitable co-solvents are $C_1$-$C_6$-alkyl alcohols and ethers and mixtures thereof. The co-solvent may constitute 5 to 40% w/w of the formulation, though preferably less than 20% w/w of the formulation. Antioxidant stabilisers may be incorporated in such solutions-formulations to inhibit deterioration of the active ingredient and are conveniently alkali metal ascorbates or bisulphites. They are preferably present in an amount of up to 0.25% w/w of the formulation.

Such self-propelling formulations may be prepared by any method known in the art. For example, the active ingredient (either as particles as defined hereinbefore as such or in suspension in a suitable liquid or in up to 20% w/v solution in an acceptable co-solvent, as appropriate) is mixed with any other constituents of a pharmaceutically acceptable carrier. The resulting mixture is cooled, introduced in a suitable cooled container, and propellant is added thereto in liquid form; and the container is sealed. Alternatively, such self-propelling formulations may be prepared by mixing the active ingredient either in particles as hereinbefore defined or in 2 to 20% w/v alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container at ambient temperature through a valve which comprises a part of the container and is used to control release of the formulation from it. Desirably, the container is purged by removing air from it at a convenient stage in the preparation of the self-propelling formulation.

A suitable container for a self-propelling formulation is one provided with a manually-operable valve and constructed of aluminium, stainless steel or reinforced glass. The valve should, of course, be one having the desired spray characteristics of particle size as hereinbefore defined. Advantageously, the valve is of the type which delivers a fixed amount of the formulation on the occasion of each operation of the valve, for example, about 50 to 100 microliters of formulation in each delivery.

Formulations of the present invention may also be in the form of an aqueous or dilute alcoholic solution, optionally a sterile solution of the active ingredient for use in a nebuliser or atomizer, wherein an accelerated air stream is used to produce a fine mist consisting of small droplets of the solution. A buffering agent and a surface active agent may also be included in such a formulation which should also contain a preservative such as methylhydroxybenzoate.

Other formulations suitable for nasal administration include a fine powder having a particle size of 10 to 100 microns which is administered in the manner in which snuff is taken, i.e. by rapid inhalation through the nasal passage from a container of the powder held close up to the nose.

In addition to the aforementioned ingredients, the formulations of this invention may include one or more additional ingredients, such as diluents, buffers, flavouring agents, binders, surface active agents, thickeners, lubricants, preservatives, e.g. methylhydroxybenzoate (including anti-oxidants), emulsifying agents and the like.

The compositions may further contain other therapeutically active compounds usually applied in the treatment of the above mentioned pathological conditions, for instance glucocorticoids, anti-histamines, platelet activating factor (PAF) antagonists, anticholinergic agents, methyl xanthines, $\beta$-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

According to the invention, the present compounds are administered to a patient suffering from one of the above mentioned pathological conditions in a daily dose (for adults) from 0.1 mg to 7000 mg, preferably from 35–3500 mg, and in the veterinary practice correspondingly in daily doses from 0.5 to 100 mg/kg bodyweight.

The invention will now be further described in the following non-limiting Examples:

EXAMPLE 1

3-(2'-Quinolylmethoxy)-N-(3''-carboxymethoxybenzyl)aniline

To a solution of 3-(2'-quinolylmethoxy)aniline (2.5 g, 10 mmole) in methanol (100 ml), 3-formylphenoxyacetic acid (2.0 g) is added, and the mixture is stirred at ambient temperature for 1 hour. The precipitated 3-(2'-quinolylmethoxy)-N-(3''-carboxymethoxybenzylidene)aniline is collected by filtration, washed with a minor amount of methanol and with diethyl ether and dried in air. It is then suspended in ethanol (200 ml), and sodium borohydride (1.5 g) is added in portions during 1 hour, while stirring at ambient temperature. The resulting mixture is filtered through filter aid and evaporated in vacuo. The residue is treated with water, and the resulting solution is neutralized to pH 7.0 using dilute acetic acid. It is then extracted twice with ethyl acetate (about 150 ml), and the organic layer is separated, dried (MgSO$_4$) and evaporated in vacuo to give the title compound, which after recrystallization from ethanol is obtained with a melting point of 122°–124° C. dec.

TABLE I

Examples 2–16
By following the procedure of Example 1 and using the appropriate starting materials, compounds of Table I are obtained.

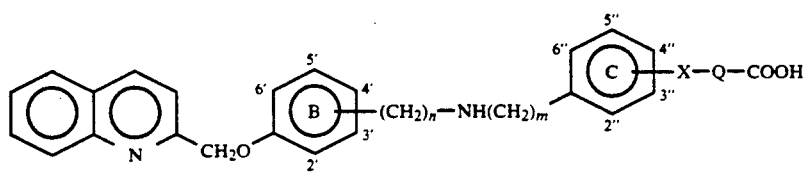

| Ex. No. | Position of bond in ring B | Position of bond in ring C | n | m | X | Q | Melting point | Remarks |
|---|---|---|---|---|---|---|---|---|
| 2 | 3' | 2'' | 1 | 0 | bond | bond | 168–170° C. | |

TABLE I-continued

Examples 2-16
By following the procedure of Example 1 and using the appropriate starting materials,
compounds of Table 1 are obtained.

| | | | n | m | X | Q | | |
|---|---|---|---|---|---|---|---|---|
| 3 | 3' | 3" | 1 | 0 | bond | bond | 166-168° C. | |
| 4 | 3' | 4" | 1 | 0 | bond | bond | 180-182° C. | hydrate |
| 5 | 4' | 4" | 1 | 0 | bond | bond | >240° C. | sodium salt, dihydrate |
| 6 | 3' | 4" | 1 | 1 | bond | bond | 175-177° C. | dihydrate |
| 7 | 4' | 4" | 1 | 1 | bond | bond | 225-227° C. | |
| 8 | 3' | 4" | 1 | 0 | bond | —CH$_2$— | 138-140° C. | hemihydrate |
| 9 | 3' | 2" | 0 | 1 | oxygen | —CH$_2$— | 151-152° C. | |
| 10 | 3' | 4" | 0 | 1 | oxygen | —CH$_2$— | 195-235° C. | sodium salt, trihydrate |
| 11 | 3' | 2" | 0 | 1 | oxygen | —(CH$_2$)$_2$— | 80-85° C. | hydrate |
| 12 | 3' | 4" | 0 | 1 | oxygen | —CH(CH$_3$)— | 187-189° C. | dihydrochloride, hydrate |
| 13 | 4' | 2" | 0 | 1 | oxygen | —CH(CH$_3$)— | 175-179° C. | dihydrochloride, trihydrate |
| 14 | 3' | 2" | 0 | 1 | oxygen | —(CH$_2$)$_3$— | 137-138° C. | |
| 15 | 3' | 3" | 0 | 1 | oxygen | —(CH$_2$)$_3$— | 160-162° C. | dihydrochloride, hydrate |
| 16 | 3' | 4" | 0 | 1 | oxygen | —(CH$_2$)$_3$— | 155-170° C. | dihydrochloride, hemihydrate |

Pharmacological Data

| Compound | | IC$_{50}$ | pK$_B$ |
|---|---|---|---|
| prior art ref. 1 | 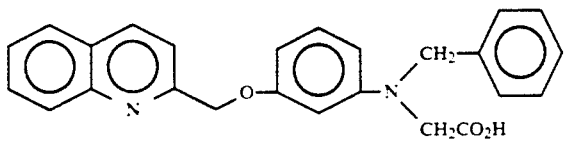 | 0.04 μM | |
| ref. II example 38 | 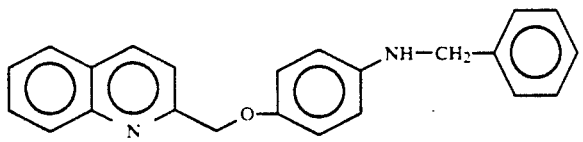 | 0.9 μM | |
| example 39 | 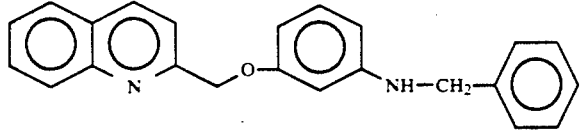 | 0.03 μM | 6.9 |
| example 67 | 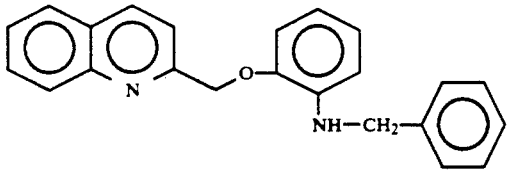 | >10 μM | |
| invention example 1 | 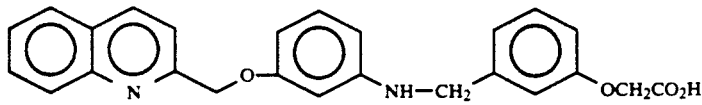 | | 8.3 |
| example 9 | 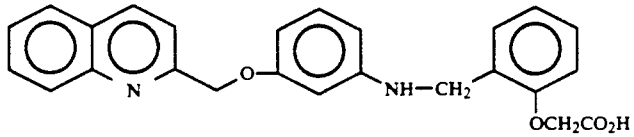 | 0.016 μM | 9.5 |

TABLE I-continued

Examples 2-16
By following the procedure of Example 1 and using the appropriate starting materials, compounds of Table 1 are obtained.

| | |
|---|---|
| example 10 | 8.4 |

EXAMPLE 17

3-(2'-Quinolylmethoxy)-N-(4''-(1H-tetrazolyl)benzyl)aniline

A mixture of 3-(2'-quinolylmethoxy)-N-(4''-cyanobenzyl)aniline (0.75 g, 2 mmole), sodium azide (0.5 g), ammonium chloride (0.2 g) and dimethyl formamide (15 ml) is stirred at 120° C. for 5 hours. The resulting mixture is, after cooling, carefully poured into a mixture of ice and water, whereafter an excess of dilute acetic acid is added to precipitate the title compound. It is collected by filtration and dissolved in an equimolar amount of dilute potassium hydroxide. After evaporation in vacuo and reevaporation several times with ethanol, the residue is triturated with isopropanol to give the potassium salt of the title compound as a dihydrate having a melting point higher than 250° C.

EXAMPLE 18

3-(2'-Quinolylmethoxy)-N-(3''-(1H-tetrazolyl)benzyl)aniline

By following the procedure of Example 17, but replacing 3-(2'-quinolylmethoxy)-N-(4''-cyanobenzyl)aniline with 3-(2'-quinolylmethoxy)-N-(3''-cyanobenzyl)aniline, the title compound is obtained as a hydrate with a melting point of 116°-118° C.

EXAMPLE 19

3-(2'-Quinolylmethoxy)-N-(4''-(1H-tetrazolyl)(3-propyloxy)benzyl)aniline

By following the procedure of Example 17, but replacing 3-(2'-quinolylmethoxy)-N-(4''-cyanobenzyl)aniline with 3-(2'-quinolylmethoxy)-N-(4''-cyano(3-propyloxy)benzyl)aniline, the title compound is obtained as a dihydrate of the dihydrochloride with a melting point of 115°-117° C.

EXAMPLE 20

3(2'-Quinolylmethoxy)-N-(3''-fluorobenzyl)-N-(4'''-hydroxaminocarbonylbenzyl)aniline A mixture of 3-(2'-quinolylmethoxy)-N-(3''-fluorobenzyl)-N-(4'''-carbomethoxybenzyl)aniline (2.4 g, 4.7 mmole), hydroxylamine hydrochloride (1.4 g, 20 mmole), 6.2N potassium hydroxide (5 ml) and methanol (25 ml) is stirred at ambient temperature for about 48 hours. The resulting solution is then acidified using 4N acetic acid to precipitate the title compound which is obtained as a hemihydrate with a melting point of 157°-160° C.

EXAMPLE 21

3-(2'-Quinolylmethoxy)-N-(2''-hydroxaminocarbonylphenyl)-aniline

By following the procedure of Example 20, but replacing 3-(2'-quinolylmethoxy)-N-(3''-fluorobenzyl)-N-(4'''carbomethoxybenzyl)aniline with 3-(2'-quinolylmethoxy)-N-(2''-carbethoxyphenyl)aniline, the title compound is obtained with a melting point of 184°-187° C.

EXAMPLE 22

4-(2'-Quinolylmethoxy)-N-(2''-carboxymethoxybenzyl)-aniline

By following the procedure of Example 1, but replacing 3-(2'-quinolylmethoxy)aniline with 4-(2'-quinolylmethoxy)aniline and 3-formylphenoxyacetic acid with 2-formylphenoxyacetic acid, the title compound is obtained as a dihydrochloride, pentahydrate with a melting point 215°-217° C.

What we claim is:

1. A compound of the formula I

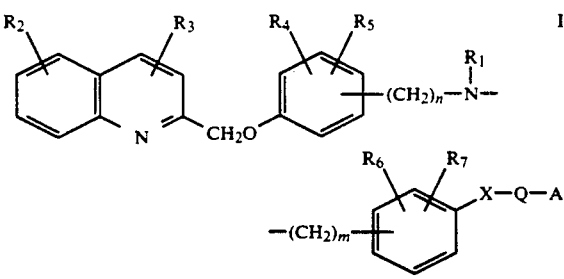

in which formula I $R^1$ stands for hydrogen, straight or branched saturated or unsaturated $C_1$-$C_8$-alkyl, aryl or for ar-$C_1$-$C_4$-alkyl wherein aryl and ar are phenyl, the said alkyl and phenyl being unsubstituted or substituted by halogen, trifluoro methyl, cyano, nitro, amino, carboxy, carbalkoxy, carbamyl, hydroxy, alkyl or alkoxy; $R_2$, $R_3$, $R_4$, $R_5$, $R_6$ and $R_7$ are the same or different and stand for hydrogen, halogen, pseudo halogen, cyano, nitro, amino, carboxy, carbalkoxy, carbamyl, hydroxy, alkyl or alkoxy; n and m are the same or different and stand for an integer from 0-6; provided that n cannot be zero when A stands for carboxy and X and Q both stand for a bond; X stands for a bond or for O, S, S(O), $S(O)_2$ or for $NR_8$ where $R_8$ is defined as $R_1$ above; Q stands for a bond or for straight or branched, $C_1-C_6$-alkylene; A stands for carboxy, 1H-tetrazolyl, a sulphonic acid group, a sulfamyl group, a sulphinic acid group or a hydroxamic acid group, and pharmaceutically acceptable, non-toxic salts thereof.

2. A compound according to formula I of claim 1, in which —X—Q—A stands for a carboxy-$C_1-C_6$-alkoxy or a 1H-tetrazolyl group.

3. A salt according to claim 1, in which the salt is selected from the group consisting of salts formed with hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid, and alkali metal salts and alkaline earth metal salts, salts with ammonia, $C_1-C_6$alkylamines, $C_1-C_6$-alkanolamines, procaine, cycloalkylamines, benzylamines, morpholine and N-ethylpiperidine.

4. A compound of claim 1 which is selected from the group consisting of 3-(2'-quinolylmethoxy)-N-(3''-carboxymethoxybenzyl)aniline;
3-(2'-quinolylmethoxy)-N-(2''-carboxymethoxybenzyl)aniline;
3-(2'-quinolylmethoxy)-N-(4''-carboxymethoxybenzyl)aniline;
3-(2'-quinolylmethoxy)-N-(4''-(1-carboxyethoxy)benzyl)aniline;
3-(2'-quinolylmethoxy)-N-(2''-carboxy-(3-propyloxy)benzyl)aniline;
3-(2'-quinolylmethoxy)-N-(4''-(1H-tetrazolyl)benzyl)aniline;
3-(2'-quinolylmethoxy)-N-(3''-(1H-tetrazolyl)benzyl)aniline
3-(2'-quinolylmethoxy)-N-(4''-(1H-tetrazolyl)(3-propyloxy)benzyl)aniline;
3-(2'-quinolylmethoxy)-N-(3''-fluorobenzyl)-N-(4'''-hydroxaminocarbonylbenzyl)aniline.

5. A pharmaceutical composition for use in obtaining leukotriene antagonistic activity which comprises an effective amount of a compound according to claim 1, and a pharmaceutically acceptable carrier therefor.

6. A method of treating a patient in need of reduced leukotriene activity which comprises administering an effective amount of a compound according to claim 1.

* * * * *